(12) United States Patent
Charman

(10) Patent No.: US 8,501,114 B1
(45) Date of Patent: Aug. 6, 2013

(54) CURETTAGE COLLECTION APPARATUS

(76) Inventor: Howard P. Charman, Alta Loma, CA (US)

( * ) Notice: Subject to any disclaimer, the term of this patent is extended or adjusted under 35 U.S.C. 154(b) by 749 days.

(21) Appl. No.: 12/129,214

(22) Filed: May 29, 2008

(51) Int. Cl.
*B01L 3/00* (2006.01)
*B01L 99/00* (2010.01)
*A61B 10/00* (2006.01)

(52) U.S. Cl.
USPC .......................................... 422/500; 600/570

(58) Field of Classification Search
USPC .......................................................... 422/99
See application file for complete search history.

(56) References Cited

U.S. PATENT DOCUMENTS

| | | | |
|---|---|---|---|
| 3,156,305 A | 11/1964 | Nash | |
| D248,819 S | 8/1978 | Hare | |
| 4,355,432 A | 10/1982 | Storm, Jr. | |
| 5,033,156 A | 7/1991 | Stewart | |
| 5,348,023 A * | 9/1994 | McLucas | 600/570 |
| 6,012,227 A | 1/2000 | Lent | |
| 2006/0075591 A1 | 4/2006 | Goldsberry | |
| 2006/0168753 A1 | 8/2006 | Crisswell | |

* cited by examiner

*Primary Examiner* — Bobby Ramdhanie
*Assistant Examiner* — Bryan Kilpatrick

(57) ABSTRACT

A curettage collection apparatus includes a plate that has first side, a second side, and a perimeter edge. The perimeter edge includes a first edge, a second edge, a third edge and a fourth edge wherein the first and second edges are positioned opposite of each other. The first edge is convexly arcuate and the second edge is concavely arcuate. An elongated rod is attached to and extends away from the first side.

10 Claims, 3 Drawing Sheets

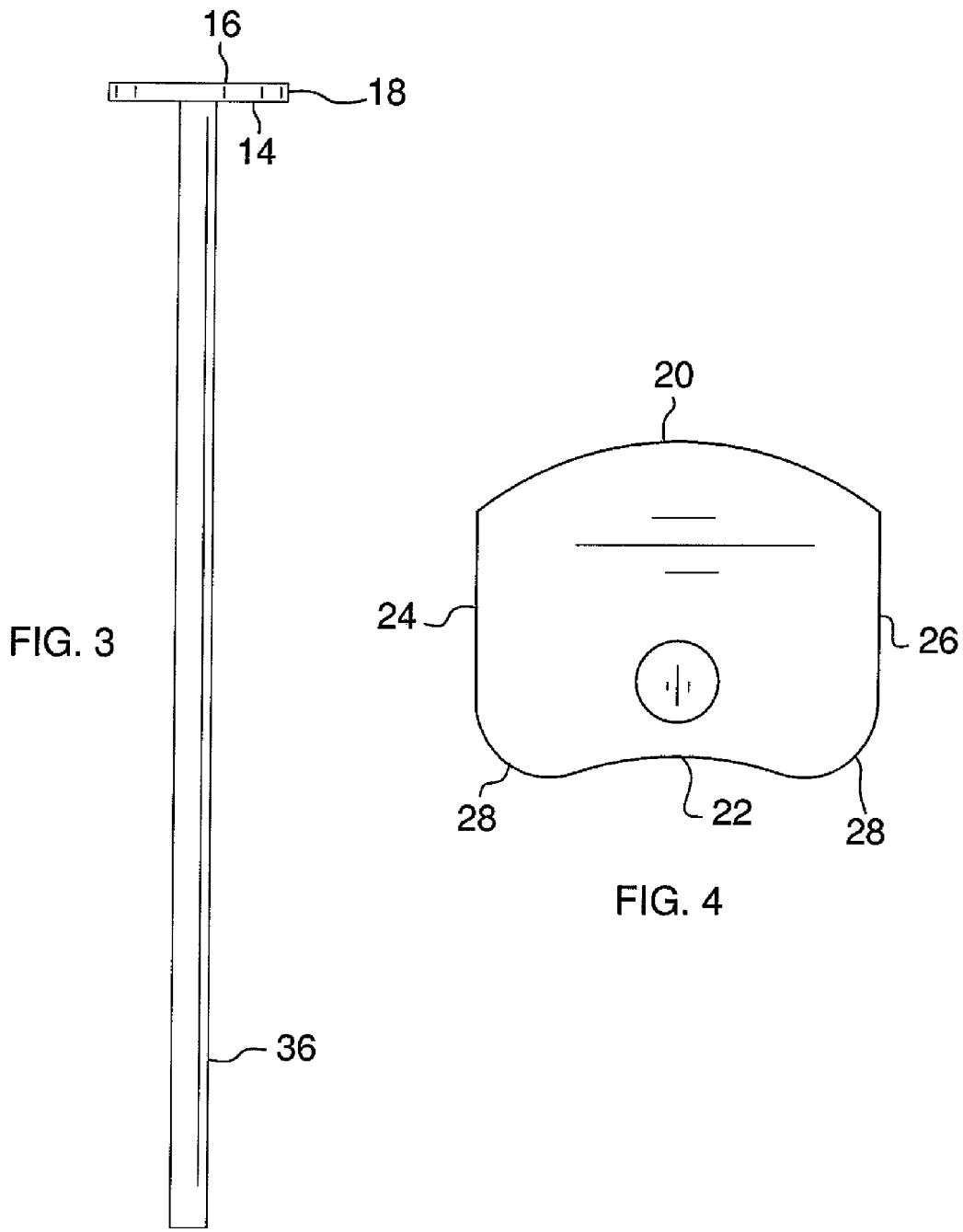

CURETTAGE COLLECTION APPARATUS

BACKGROUND OF THE INVENTION

Field of the Invention

The present invention relates to medical tissue collection tools and more particularly pertains to a new medical tissue collection tool for removing biological matter collected and captured in a tissue trap after a curettage procedure.

SUMMARY OF THE INVENTION

The present invention meets the needs presented above by generally comprising a plate that has first side, a second side, and a perimeter edge. The perimeter edge includes a first edge, a second edge, a third edge and a fourth edge wherein the first and second edges are positioned opposite of each other. The first edge is convexly arcuate and the second edge is concavely arcuate. An elongated rod is attached to and extends away from the first side.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a top view of the present invention.

FIG. 4 is a rear view of the present invention.

DESCRIPTION OF THE PREFERRED EMBODIMENT

Figure 1:
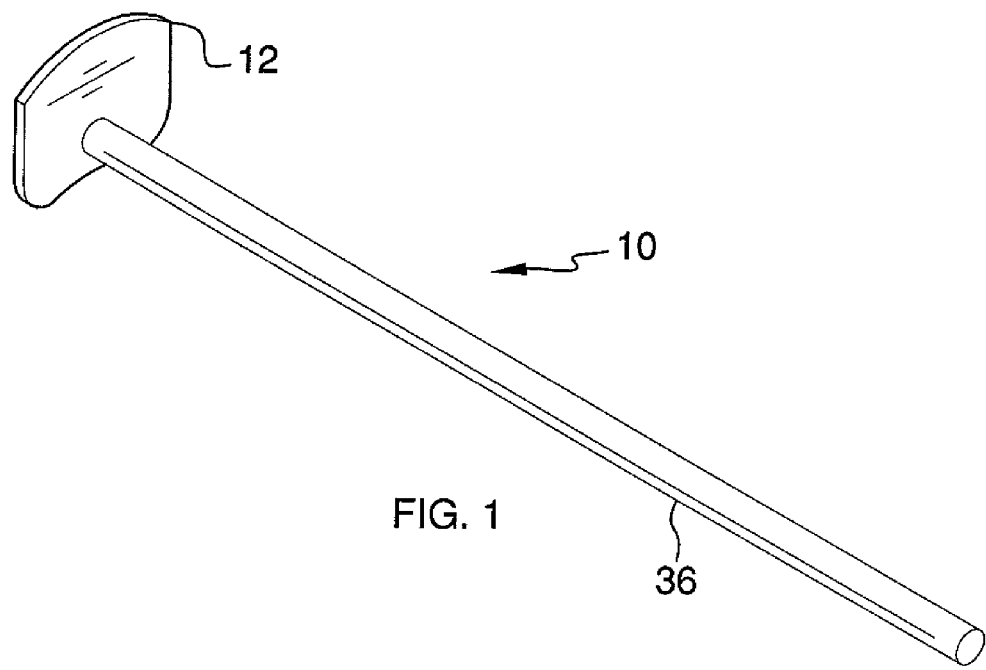
FIG. 1 is a rear perspective view of a curettage collection apparatus according to the present invention.
Figure 2:
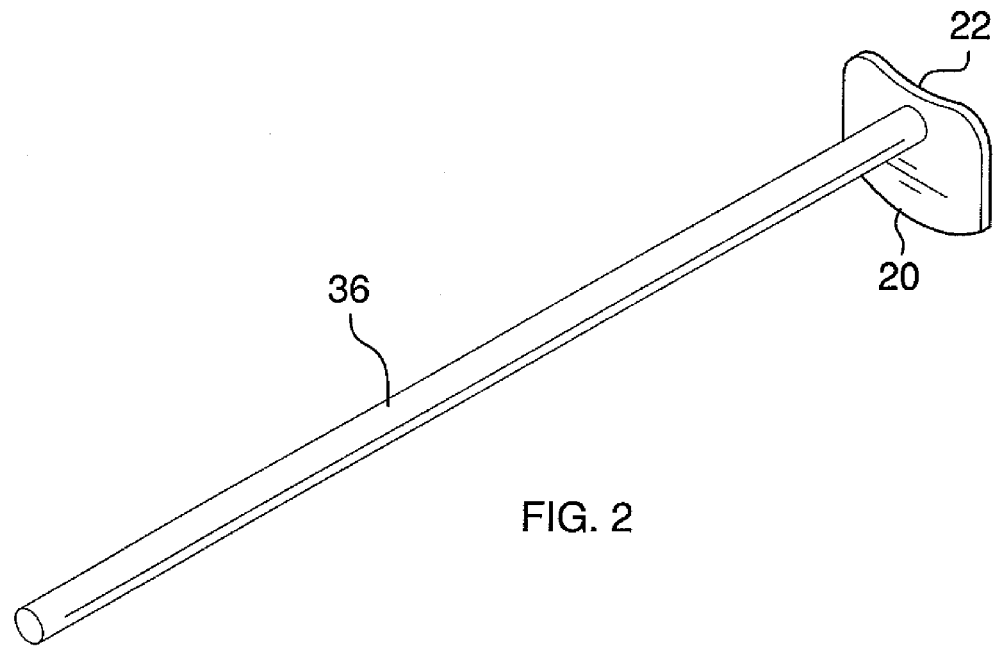
FIG. 2 is a rear perspective view of the present invention.
Figure 5:
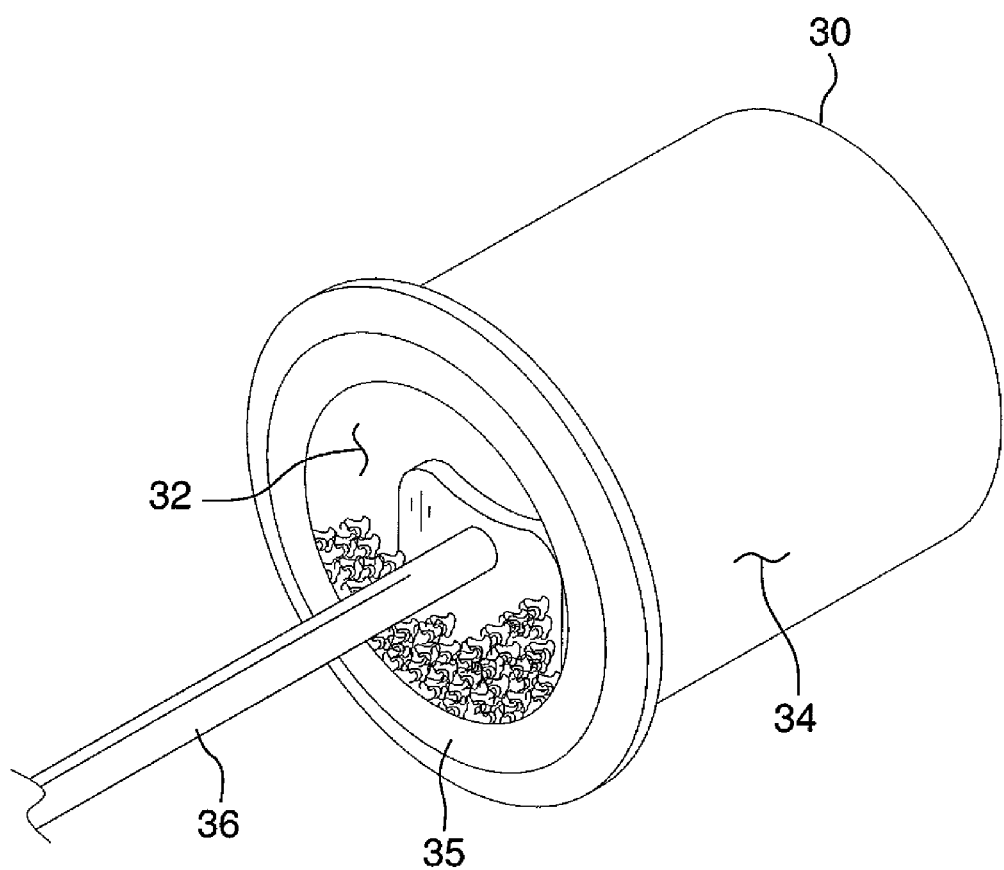
FIG. 5 is a perspective in-use view of the present invention.

With reference now to the drawings, and in particular to FIGS. 1 through 5 thereof, a new medical tissue collection tool embodying the principles and concepts of the present invention and generally designated by the reference numeral 10 will be described.

As best illustrated in FIGS. 1 through 5, the curettage collection apparatus 10 generally comprises a plate 12 that has first side 14, a second side 16, and a perimeter edge 18. The perimeter edge 18 includes a first edge 20, a second edge 22, a third edge 24 and a fourth edge 26 wherein the first 20 and second 22 edges are positioned opposite of each other. The first edge 20 is convexly arcuate and the second edge 22 is concavely arcuate. A juncture 28 of each of the third 24 and fourth 26 edges and the second edge 22 is convexly arcuate.

The plate 12 has a length from the third edge 24 to the fourth edge 26 between 1.20 inches and 1.30 inches and a height from the first edge 20 to the second edge 22 between 1.0 inches and 1.10 inches. Each of the edge 20 and second 22 edges is arcuate along a curve of a circle has a radius between 0.95 inches and 1.05 inches. Each of the junctures 28 of the second edge 22 and the third 24 and fourth 26 edges is arcuate along a curve of a circle has a radius between 0.20 inches and 0.30 inches. The plate 12 has a width from the first side 14 to the second side 16 between 0.10 inches and 0.15 inches.

The measurements provided above generally conform to the arc of a wall of a conventional tissue filter trap 30 used to collect biological tissue retained and scraped caught from a woman after conception and other like procedures. The material collected must be scraped from the trap 30 for examination purposes. The measurements of the plate 12 allow the first edge 20 to conform to an inner surface 32 of the trap 30 and the second edge 22 conforms to an outer surface 34 of the trap 30. The rounded nature of the junctures 28 of the third 24 and forth 26 edges with the second edge 22 allow for easier scraping of material along a rubber edge sealing member 35 of the trap 30.

An elongated rod 36 is attached to and extends away from the first side 14. The rod 36 is positioned nearer to the second edge 22 than the first 20 and is equally spaced from the third 24 and fourth 26 edges. The rod 36 has a length greater than 5 inches and the rod 36 is oriented perpendicular to a plane of the first side 14. The rod 36 may also be used for assisting a person in removing a sealing cover of the trap 30.

In use, the trap 30 is opened and the plate 12 is used to scrape all material from the trap 30. Typically a scalpel is used for this task but the sharpened edge thereof makes this difficult as does the angle of the scalpel blade with respect to the direction the material is being pulled from the trap 30. The plate 12 has no sharpened edges but is contoured to match the shape of the trap 30 to allow for easy and complete removal of the biological material from the trap 30.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A collection apparatus to remove curettage from a tissue trap, said apparatus comprising:
   a plate having first side, a second side, and a perimeter edge, said perimeter edge including a first edge, a second edge, a third edge and a fourth edge wherein said first and second edges are positioned opposite of each other, said first edge being convexly arcuate, said second edge being concavely arcuate; and
   an elongated rod being attached to and extending away from said first side.

2. The apparatus according to claim 1, wherein a juncture of each of said third and fourth edges and said second edge is convexly arcuate.

3. The apparatus according to claim 1, wherein said plate has a length from said third edge to said fourth edge between 1.20 inches and 1.30 inches, said plate having a height from said first edge to said second edge between 1.0 inches and 1.10 inches.

4. The apparatus according to claim 3, wherein each of said first and second edges being arcuate along a curve of a circle having a radius between 0.95 inches and 1.05 inches.

5. The apparatus according to claim 1, wherein said rod is positioned nearer to said second edge than said first and being equally spaced from said third and fourth edges.

6. The apparatus according to claim 5, wherein said rod has a length greater than 5 inches.

7. The apparatus according to claim 6, wherein said rod is oriented perpendicular to a plane of said first side.

8. The apparatus according to claim 6, wherein said plate has a length from said third edge to said fourth edge between 1.20 inches and 1.30 inches, said plate having a height from said first edge to said second edge between 1.0 inches and 1.10 inches.

9. The apparatus according to claim 8, wherein each of said first and second edges being arcuate along a curve of a circle having a radius between 0.95 inches and 1.05 inches.

10. A collection apparatus to remove curettage from a tissue trap, said apparatus comprising:
a plate having first side, a second side, and a perimeter edge, said perimeter edge including a first edge, a second edge, a third edge and a fourth edge wherein said first and second edges are positioned opposite of each other, said first edge being convexly arcuate, said second edge being concavely arcuate, a juncture of each of said third and fourth edges and said second edge being convexly arcuate, said plate having a length from said third edge to said fourth edge between 1.20 inches and 1.30 inches, said plate having a height from said first edge to said second edge between 1.0 inches and 1.10 inches, each of said first and second edges being arcuate along a curve of a circle having a radius between 0.95 inches and 1.05 inches, each of said junctures of said second edge and said third and fourth edges being arcuate along a curve of a circle having a radius between 0.20 inches and 0.30 inches, said plate having a width from said first side to said second side between 0.10 inches and 0.15 inches; and an elongated rod being attached to and extending away from said first side, said rod being positioned nearer to said second edge than said first and being equally spaced from said third and fourth edges, said rod having a length greater than 5 inches, said rod being oriented perpendicular to a plane of said first side.

* * * * *